United States Patent
Abrahams et al.

(10) Patent No.: US 9,387,029 B2
(45) Date of Patent: Jul. 12, 2016

(54) SPRING SCREW APPARATUSES AND METHODS OF USING SAME

(75) Inventors: John M. Abrahams, Scarsdale, NY (US); Peter J. Amarosa, Dover, NH (US); Michael Leatherman, Dover, NH (US)

(73) Assignee: Asilo Medix, Inc., Dover, NH (US)

(*) Notice: Subject to any disclaimer, the term of this patent is extended or adjusted under 35 U.S.C. 154(b) by 229 days.

(21) Appl. No.: 12/971,579

(22) Filed: Dec. 17, 2010

(65) Prior Publication Data

US 2012/0158069 A1    Jun. 21, 2012

(51) Int. Cl.
| | |
|---|---|
| A61B 17/04 | (2006.01) |
| A61B 17/86 | (2006.01) |
| A61F 2/08 | (2006.01) |
| A61B 17/80 | (2006.01) |
| A61B 17/88 | (2006.01) |
| A61B 17/70 | (2006.01) |

(52) U.S. Cl.
CPC ......... *A61B 17/8685* (2013.01); *A61B 17/8038* (2013.01); *A61B 17/888* (2013.01); *A61B 17/70* (2013.01); *A61B 17/8883* (2013.01)

(58) Field of Classification Search
CPC ............ A61B 17/8038; A61B 17/888; A61B 17/8883; A61B 17/8685; A61B 2017/867; A61B 17/80

USPC ........... 606/300–331, 286, 290, 291; 411/21, 411/347
See application file for complete search history.

(56) References Cited

U.S. PATENT DOCUMENTS

| 231,588 | A | * | 8/1880 | Kernochan ...................... 411/81 |
|---|---|---|---|---|
| 2,718,252 | A | * | 9/1955 | Schuster ........................ 411/322 |
| 5,478,342 | A | * | 12/1995 | Kohrs ............................. 606/310 |
| 2003/0053880 | A1 | * | 3/2003 | Johansson et al. .............. 411/21 |
| 2006/0200147 | A1 | * | 9/2006 | Ensign et al. .................... 606/69 |
| 2009/0192553 | A1 | * | 7/2009 | Maguire et al. ................ 606/305 |
| 2012/0022593 | A1 | * | 1/2012 | Kovach et al. ................. 606/264 |

* cited by examiner

*Primary Examiner* — Kevin T Truong
*Assistant Examiner* — Si Ming Ku
(74) *Attorney, Agent, or Firm* — McHale & Slavin, P.A.

(57) ABSTRACT

Disclosed is a locking spring screw formed from a cylindrical screw body having a screw head that includes a tool slot adapted for receipt of a flexible spring member. The tool slot includes at least one outlet formed adjacent to the tool slot which is adapted for passage therethrough of a tongue extending outwardly from the spring member. A ridge is located opposite the outlet from the cylindrical screw body and formed at least partially around the circumference of the screw head wherein the spring member is retracted during installation and, upon the ridge engaging a flange, the spring member is released preventing screw head removal by entrapping the flange between the ridge and the tongue of the spring member.

11 Claims, 6 Drawing Sheets

SPRING SCREW APPARATUSES AND METHODS OF USING SAME

RELATED APPLICATIONS

This application is related to an application entitled "Spinal Implant Apparatuses and Methods of Implanting and Using Same", filed on the same date of Dec. 17, 2010 in the United States Patent and Trademark Office, with the same named inventors, the disclosure of which is incorporated herein by reference.

BACKGROUND OF THE INVENTION

Implants are widely used to replace a missing biological structure, support a damaged biological structure, or enhance an existing biological structure. Medical implants are man-made devices, in contrast to a transplant, which is a transplanted biomedical tissue. The surface of implants that contact the body might be made of a biocompatible material such as titanium or silicone depending on what is the most functional. In the case of orthopedic implants, like spinal implants, the manner in which the implant is attached to the patient is an important consideration.

In many situations, screws are used to secure the implant to hard tissue (e.g. bone) of the patient. One consideration in using screws during orthopedic implantation procedures is ensuring proper screw orientation with respect to the implant when the screw is advanced into the bone. Another consideration is easing the implantation process for an attending medical professional, for example a surgeon installing the implant.

SUMMARY OF THE INVENTION

An aspect of an embodiment of the invention relates to providing a locking spring screw with a spring member which locks the screw into place with respect to an implantable device while still being able to rotate for attaching the implantable device to an implantation site. In an embodiment of the invention, the implantable device is provided with at least one screw hole, a portion of which is adapted to act as a counterpart to components of the spring screw in order to lock the screw into place with respect to the implantable device. For example, in an embodiment of the invention a portion of the screw hole is adapted to provide a flange which acts as a counterpart to a flange slot created by components of the screw, wherein the flange fits within the flange slot, locking the spring screw substantially within a plane but still allowing rotation of the screw about its vertical axis. In an embodiment of the invention, a spring member is used as at least one of the components for creating the flange slot in which the flange fits. In an embodiment of the invention, a ridge on the head of the screw forms a side of the flange slot opposite the spring member.

In an embodiment of the invention, the spring screw and the implantable device are jointly adapted to provide the screw with substantial movement in only one degree of freedom once locked into the implantable device. Optionally, the one degree of freedom is around the vertical axis of the screw.

In an embodiment of the invention, the spring member is inserted into a tool slot provided to the head of the spring screw in a flexed state and upon insertion into the tool slot, the spring member assumes an expanded state. Optionally, the spring member is placed into the head of the spring screw during manufacture. Optionally, the spring member is provided with at least one tongue which protrudes through an outlet located on the screw head thereby securing the spring member to the screw head.

In an embodiment of the invention, the outlet is located on the screw head above the floor of the tool slot such that the spring member can be flexed towards the floor by a tool. In an embodiment of the invention, the distance the spring member can flex towards the floor and the length of the at least one tongue are correlated to allow for the spring screw to be inserted into the screw hole (while the spring member is flexed) but not to allow the spring member to slip out of the outlet towards the vertical axis of the screw.

In an embodiment of the invention, the tool slot also doubles as the interface between the screw and the tool used by the attending medical professional to tighten or loosen the screw with respect to the implantation site. In some embodiments of the invention, the tool slot shape and/or size is varied to accommodate different tools. In some embodiments of the invention, the spring member shape and/or size is varied to accommodate different sized tool slots.

In an embodiment of the invention, the cylindrical body of the spring screw is adapted to be driven into an implantation site. For example, the body is provided with threading. In some embodiments of the invention, the implantation site is comprised of hard body tissue, such as bone. Optionally, the spring member remains flexed while the tool is used to drive the screw into the implantation site.

A further aspect of an embodiment of the invention relates to a method of using a screw provided with a spring member to secure an implantable device to an implantation site. In an embodiment of the invention, the method uses a screw adapted to lock the screw into place with respect to an implantable device while still allowing the screw to rotate for attaching the implantable device to the implantation site. In an embodiment of the invention, the screw is inserted in a screw hole located on the implantable device while the spring member is flexed towards the floor of a tool slot in the screw head using a tool. In an embodiment of the invention, the screw is advanced fully until a ridge of the head of the screw abuts a flange of the screw hole. The spring member is released by the tool which results in expansion of the spring member such that a tongue portion of the spring member extends out of an outlet in the screw head, trapping the flange of the screw hole in a flange slot formed in between the tongue portion of the spring member and the ridge of the screw head.

In an embodiment of the invention, the spring screw is substantially prohibited from moving linearly along its vertical, central axis, however the spring screw is still permitted to rotate around its central axis, for example to be screwed into the implantation site. In some embodiments of the invention, the tool is used to screw the spring screw into the implantation site, thereby securing the implant to the implantation site, while the spring member is still flexed.

In some embodiments of the invention, a plurality of spring screws is locked to an implantable device where it is desirable to attach the implantable device to the implantation site at a plurality of locations.

In an embodiment of the invention, the implantable device is placed over the implantation site with the at least one screw positioned over a location at the implantation site where it is to be secured to the patient's anatomy. The screw is then turned, drawing the implantable device towards the patient's anatomy until the implantable device is in the desired position relative to the patient. Optionally, the at least one screw is turned until the implantable device abuts the patient's anatomy.

In an embodiment of the invention, the implantation site is a vertebra. In some embodiments of the invention, a location is a pedicle of the vertebra. In some embodiments of the invention, a location is a facet of the vertebra. In some embodiments of the invention, a location is a lateral mass of the vertebra.

An aspect of an embodiment of the invention relates to a system for interlocking a screw and an implant. In an embodiment of the invention, the system comprises a spring member on the screw which in part defines a flange slot which acts as a counterpart to a flange on the implant, wherein when the flange is inserted into the flange slot, the screw and implant are interlocked.

There is therefore provided in an embodiment of the invention, a locking spring screw, comprising: a cylindrical screw body; a flexible spring member; and, a screw head attached to the cylindrical screw body, wherein the screw head comprises a tool slot adapted for receipt of the spring member, at least one outlet adjacent to the tool slot adapted for passage therethrough of a tongue of the spring member, and, a ridge located opposite the at least one outlet from the cylindrical screw body and at least partially around the circumference of the screw head.

In an embodiment of the invention, the cylindrical screw body is threaded.

In an embodiment of the invention, the tongue of the spring member and the ridge form a slot when the tongue is passed through the outlet.

In an embodiment of the invention, the length of the spring member is correlated to the amount of spring member flex allowed by a floor of the tool slot such that upon maximum flex of the spring member towards the floor, the tongue retracts at least partially into outlet.

In an embodiment of the invention, the maximum flex is no more than 20 thousandths of an inch.

In an embodiment of the invention, the tool slot and the spring member are formed as counterparts.

In an embodiment of the invention, the tongue and outlet diameter are narrower than the spring member.

In an embodiment of the invention, the ridge is sloped, increasing in size moving away from the cylindrical screw body.

In an embodiment of the invention, the at least one of the flexible spring member, cylindrical screw body and screw head are constructed of at least one of titanium, stainless steel, cobalt chrome, ceramic, polymer, or PEEK Optima.

In an embodiment of the invention, the screw length along its central axis is 8.0 mm-60.0 mm.

In an embodiment of the invention, the screw head is 3.5 mm-9.0 mm in diameter.

There is further provided in accordance with an exemplary embodiment of the invention, a system for interlocking a screw and an implant wherein the screw has motion in only one degree of freedom, comprising: an implant provided with at least one screw hole provided with a flange; and, a spring screw comprising a flexible spring member, and, a screw head attached to the cylindrical screw body, wherein the screw head comprises a tool slot adapted for receipt of the spring member, at least one outlet adjacent to the tool slot adapted for passage therethrough of a tongue of the spring member, and, a ridge located opposite the at least one outlet from the cylindrical screw body and at least partially around the circumference of the screw head, wherein when the spring member is un-flexed the tongue and the ridge form a flange slot adapted for receipt of the flange therein.

In an embodiment of the invention, the system further comprises a tool adapted to be a counterpart to the tool slot.

In an embodiment of the invention, the tool is provided with a tool hub for flexing the spring member upon insertion of the tool into the tool slot.

In an embodiment of the invention, the tool is provided with at least one ridge for providing torque to the spring screw for attaching the spring screw to the implantation site. In some embodiments of the invention, length of the spring member is correlated to the amount of spring member flex allowed by a floor of the tool slot such that upon maximum flex of the spring member towards the floor, the tongue retracts at least partially into outlet allowing tongue to pass flange. In some embodiments of the invention, the one degree of freedom is around a central axis of the spring screw.

There is further provided in accordance with an exemplary embodiment of the invention, a method of using a spring screw provided with a spring member to secure an implantable device to an implantation site, comprising: inserting the spring screw in a screw hole located on the implantable device while the spring member is flexed towards the floor of a tool slot in the screw head using a tool; advancing the spring screw until a ridge of the screw head abuts a flange of the screw hole; driving the spring screw into the implantation site; retracting the tool from the spring screw, resulting in expansion of the spring member such that a tongue portion of the spring member extends out of an outlet in the screw head, trapping the flange of the screw hole in a flange slot formed in between the tongue portion of the spring member and the ridge of the screw head.

In an embodiment of the invention, the method further comprises repeating inserting, advancing, driving and retracting for a plurality of spring screws.

In an embodiment of the invention, trapping the flange of the screw in the flange slot substantially restricts the spring screw to movement in only one degree of freedom, around its central axis.

In an embodiment of the invention, the implantation site is at least one of a vertebra, a pedicle of the vertebra, a facet of the vertebra, or a lateral mass of the vertebra.

These and other features and their advantages will be readily apparent to those skilled in the art of spinal implants from a careful reading of the Detailed Description of Exemplary Embodiments, accompanied by the following drawings.

BRIEF DESCRIPTION OF THE DRAWINGS

Embodiments of the invention are herein described, by way of example only, with reference to the accompanying drawings. In this regard, the description taken along with the drawings makes apparent to those skilled in the art how embodiments of the invention may be practiced. It should also be understood that drawings may not be to scale. In the figures.

DETAILED DESCRIPTION OF EXEMPLARY EMBODIMENTS

Throughout the application, reference is made to flexed spring member 106*a* and/or un-flexed spring member 106*b*, it should be understood that these references are to the same structural element which takes two forms depending on its current state of usage with spring screw 100. In some portions of the application, the spring member is assigned reference number 106, it should be understood that in such instances "spring member 106" is referring to the element generally, whether flexed 106*a* or un-flexed 106*b*.

Figures 1, 2:
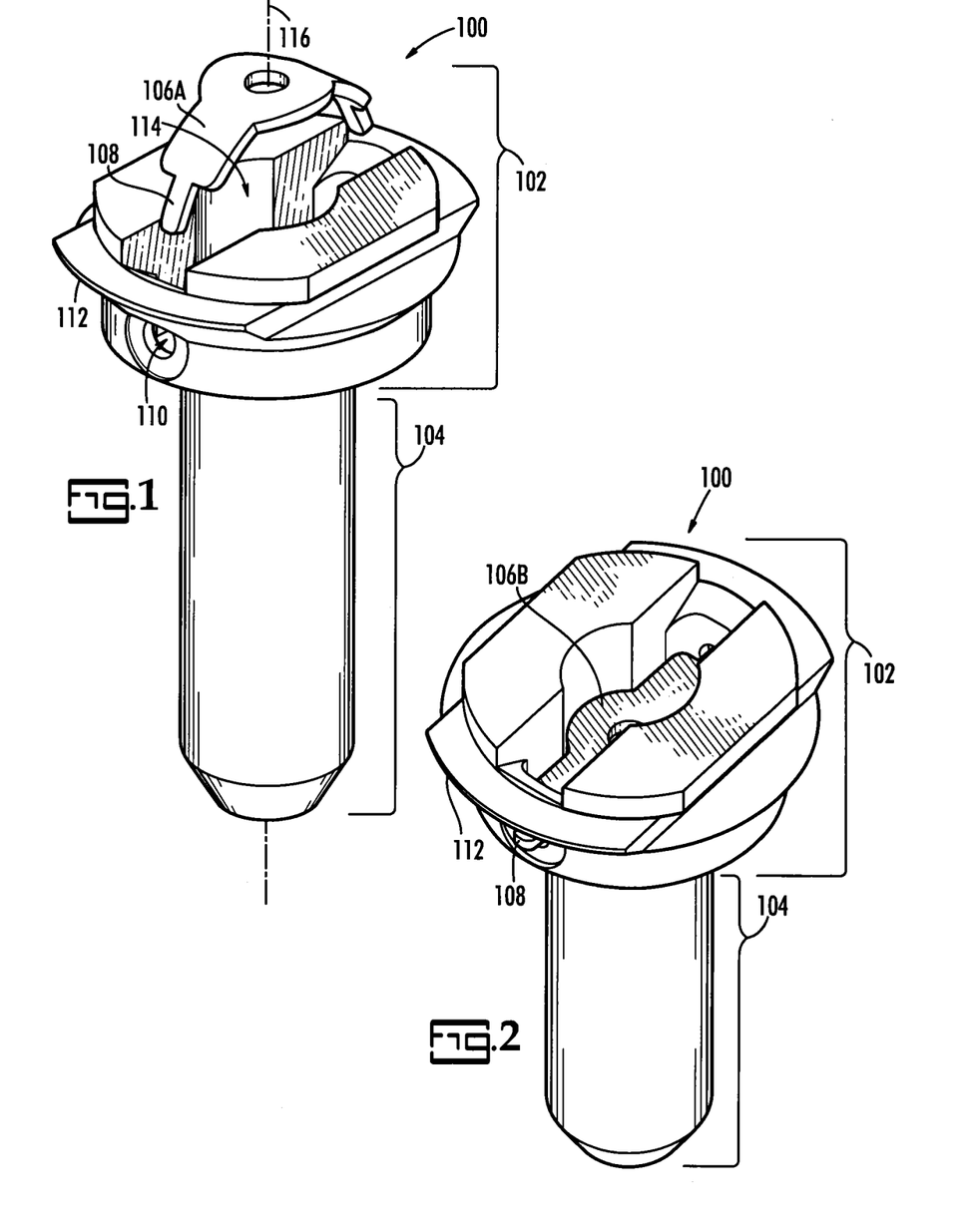
FIG. 1 is a perspective view of a spring screw with a flexed spring member, in accordance with an exemplary embodiment of the invention.
FIG. 2 is a perspective view of a spring screw with an expanded spring member, in accordance with an exemplary embodiment of the invention.

FIG. 1 is a perspective view of a spring screw 100 with a flexed spring member 106*a*, in accordance with an exemplary embodiment of the invention. In an embodiment of the invention, spring screw 100 is comprised of at least two general sections, a screw head 102 and a cylindrical body 104. The cylindrical body 104, as with most conventional screws, is the portion of the screw which is driven in to a specific attachment location at the implantation site. In some embodiments of the invention, cylindrical body 104 is provided with threading. Optionally, the threading is adapted for the type of material into which the screw will be driven.

Screw head 102 is provided with a tool slot 114 which is adapted for receipt of spring member 106*a* and/or to interface with a tool used for tightening and/or loosening the screw with respect to the attachment location, in an embodiment of the invention. Spring member 106*a* is shown flexed in FIG. 1, but it should be understood that in an embodiment of the invention, the spring member is adapted to be elastically deformed for insertion into tool slot 114 during manufacture and/or flexing during the insertion of the spring screw 100 into a spinal implant 400, shown and described in more detail with respect to FIG. 4. In an embodiment of the invention, upon insertion into tool slot 114, the spring member 106 returns to its un-flexed form 106*b*, such as shown and described with respect to FIGS. 2 and 3.

In an embodiment of the invention, spring member 106 is provided with an enlarged portion, shaped like a circle in FIGS. 1 and 2, which prevents spring member 106 from sliding out of the at least one outlet 110. Alternatively, additionally and/or optionally, spring member 106 is designed to be wider than outlet 110, except the tongue 108, which prevents spring member 106 from sliding out of outlet 110. IN an embodiment of the invention, the spring screw 100 is designed with a tight tolerance between the tool slot 114 and the enlarged portion of spring member 106. Optionally, the tolerance is about +/−1.5 thousands of an inch, to make sure that the screw will lock on both sides. Other shapes are usable, besides circular, in alternative embodiments of the invention.

A ridge 112 is provided to screw head 102 at a level where it is desired that the screw be prevented from any further insertion into the screw hole 402, in an embodiment of the invention. In some embodiments of the invention, the ridge 112 is shaped to match a flange 404 of the screw hole 402, the flange 404 shown and described in more detail with respect to FIGS. 4 and 6. For example, in an embodiment of the invention, the ridge 112 and flange 404 of the screw hole 402 are each sloped to act as complementary parts preventing over-insertion of the spring screw 100 through the screw hole 402 and/or also providing a slidable interface between the two to allow for rotation of the spring screw 100 about its vertical axis 116.

Spring member 106 is provided with at least one tongue 108 which is adapted for insertion into an outlet 110 located on screw head 102, in an embodiment of the invention. Outlet 110 is positioned on screw head 102 such that when screw head 102 is advanced fully into the screw hole 402, the outlet 110 is positioned below the level of ridge 112, in an embodiment of the invention. Thus, in an embodiment of the invention, when tongue 108 protrudes out of outlet 110 it creates a space between the tongue 108 and the ridge 112 for insertion of the flange 404. In an embodiment of the invention, tongue 108 is narrower than the outlet 110 but overall spring member 106 is wider than outlet 110 so that spring member 106 cannot completely slide out of outlet 110, only tongue 108 can.

FIG. 2 is a perspective view of spring screw 100 with an expanded spring member 106*b* placed within slot 114, in accordance with an exemplary embodiment of the invention. From this perspective, it can be seen that in some embodiments of the invention, slot 114 and spring member 106 are shaped as counterparts such that spring member 106 fits snugly within the slot 114, particularly when the spring member is in its un-flexed form 106*b*. Also seen from this perspective view is the ridge 112 on the screw head 102. In some embodiments of the invention, the ridge 112 only extends partially around the circumference of the screw head 102, such as depicted in FIG. 2, however in some embodiments of the invention, the ridge 112 could extend fully around the circumference of the screw head 102.

Figure 3:
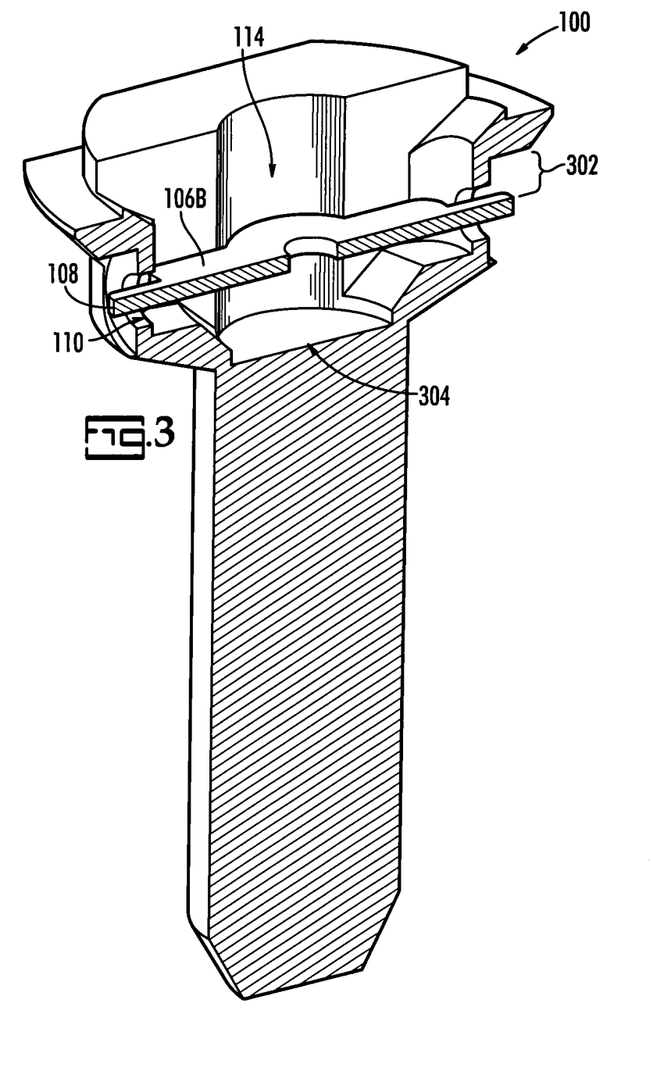
FIG. 3 is a cross-sectional view of a spring screw with an expanded spring member, in accordance with an exemplary embodiment of the invention.

FIG. 3 is a cross-sectional view of spring screw 100 with an expanded and/or un-flexed spring member 106*b*, in accordance with an exemplary embodiment of the invention. Shown in more detail is the relationship between spring member 106*b*, the at least one tongue 108 of the spring member 106 and the outlet 110 adapted for passage of the tongue 108 therethrough, in an embodiment of the invention. The at least one tongue 108 transits through the outlet 110 when spring member 106*a* un-flexes to form spring member 106*b* after insertion of the spring member 106 sufficiently deep into the slot 114. The expansion of the spring member 106 urges the at least one tongue 108 into and/or extending out of the outlet 110. It can be seen that once the at least one tongue 108 is extended through the outlet 110, a space 302 is created between the ridge 112 of the screw head 102 and the tongue 108, the space being adapted and/or sized for receipt of the flange 404, shown in more detail in FIGS. 4 and 6.

In an embodiment of the invention, spring member 106 is located above the floor 304, of the tool slot 114 to allow for the flexing of spring member 106 during placement of the spring screw 100 into the implant 400. In an embodiment of the invention, spring member 106 flexes approximately 20 thousands of an inch towards floor 304 during compression of spring member 106 by tool 800.

In an embodiment of the invention, at least a portion of spring screw 100, including spring member 106, is comprised of at least one of titanium, stainless steel, cobalt chrome, ceramic, polymer (e.g. PLA, PGA), or PEEK Optima. In some embodiments of the invention, the spring screw is 8.0 mm-60.0 mm in length along the central axis 116 and/or 3.5 mm-9.0 mm in diameter (i.e. the screw head 102). It should be understood, however, that the spring screw 100 can be scalably sized for any application and that these size ranges are merely examples.

Figure 4:
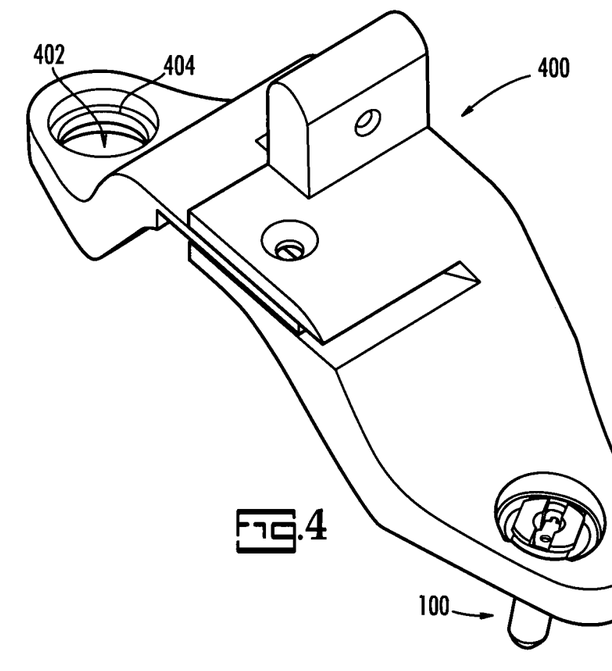
FIG. 4 is a top, perspective view of a sliding spinal implant used in conjunction with at least one spring screw, in accordance with an exemplary embodiment of the invention.

FIG. 4 is a top, perspective view of a sliding spinal implant 400 used in conjunction with at least one spring screw 100, in accordance with an exemplary embodiment of the invention. In an embodiment of the invention, flange 404 is a part of spinal implant 400, for example as shown in FIG. 4, where the flange 404 is provided around the inner circumference of screw hole 402 so that the spring screw 100 is inserted therein until the ridge 112 hits the flange 404, in an exemplary embodiment of the invention. Also shown is a spring screw 100 inserted into a screw hole 402, in an exemplary embodiment of the invention.

Figure 5:
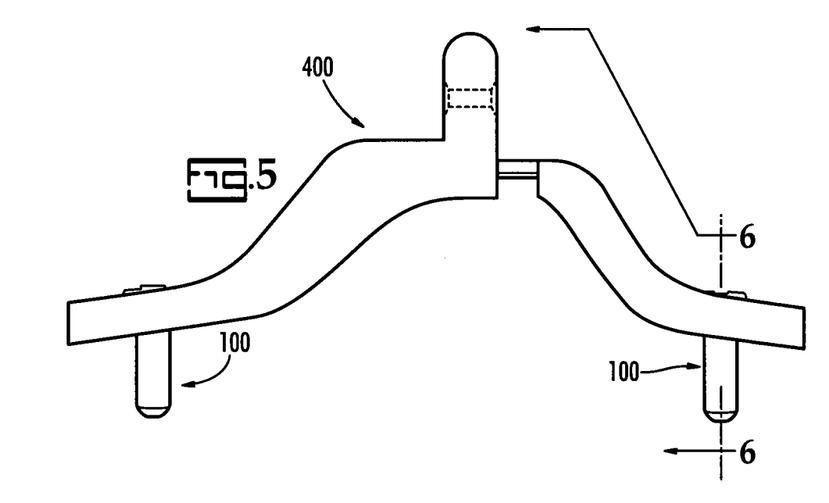
FIG. 5 is a side view of a sliding spinal implant used in conjunction with at least one spring screw, in accordance with an exemplary embodiment of the invention.

FIG. 5 is a side view of a sliding spinal implant 400 used in conjunction with at least one spring screw 100, in accordance with an exemplary embodiment of the invention. From this side view, a cross-sectional is taken, which is reflected in FIG. 6.

Figure 6:
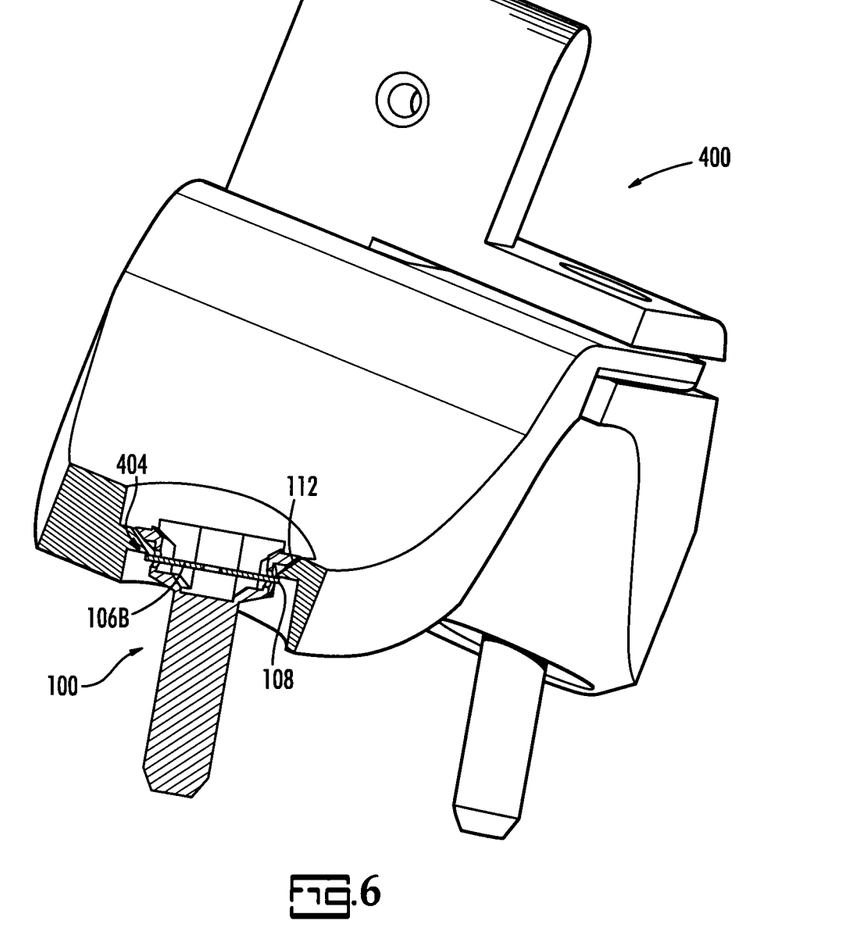
FIG. 6 is a cross-sectional view of a sliding spinal implant used in conjunction with at least one spring screw, in accordance with an exemplary embodiment of the invention.

FIG. 6 is a cross-sectional view of a sliding spinal implant 400 used in conjunction with at least one spring screw 100, in accordance with an exemplary embodiment of the invention. From this view, it can be seen that the spring member 106b and the ridge 112 form a space wherein the flange 404 of the spinal implant 400 is accommodated, in an embodiment of the invention. The ridge 112 prevents the spring screw 100 from being over-inserted into the screw hole 402 and the spring member 106 prevents the spring screw 100 from being withdrawn, in essence locking the spring screw 100 into a plane relative to the spinal implant 400.

Figure 7:
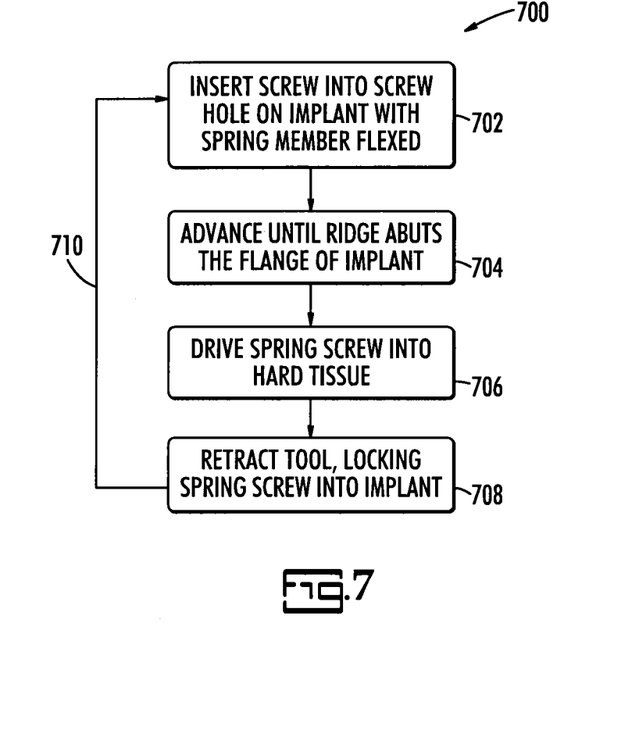
FIG. 7 is a flowchart showing a method of using a spring screw in conjunction with a spinal implant, in accordance with an exemplary embodiment of the invention.

FIG. 7 is a flowchart 700 showing a method of using a spring screw 100 in conjunction with a spinal implant 400, in accordance with an exemplary embodiment of the invention. In an embodiment of the invention, spring screw 100 is inserted (702) into screw hole 402 with the spring member 106 flexed by the tool 800, shown and described in more detail with respect to FIG. 8. Spring screw 100 is advanced (704) into screw hole 402 until ridge 112 of screw head 102 abuts flange 404 of implant 400. As described elsewhere in the application, spring screw 100 is adapted so that when ridge 112 abuts flange 404, outlet 110 is properly aligned such that when tongue 108 of un-flexed spring member 106b extends out of outlet 110, flange 404 is bracketed by tongue 108 and ridge 112.

In some embodiments of the invention, spring screw 100 is driven (706) into the hard tissue at the implantation site to attach the implant 400 to the patient, for example by using tool 800 to screw spring screw 100 into place. Optionally, spring member 106 remains flexed during the driving, although in some embodiments of the invention, the tool is retracted slightly prior to commencing the driving. Tool 800 is retracted (708) from tool slot 114, causing spring member 106 to un-flex and projecting at least one tongue 108 through outlet 110, locking spring screw 100 into a plane corresponding to the flange 404, in an embodiment of the invention.

In some embodiments of the invention, depending on how many screw holes are present on the implant and/or depending on the specific implantation needs of the implant with respect to the patient, more than one screw is used to secure the implant to the patient. Accordingly, inserting (702), advancing (704), driving (706) and retracting (708) are optionally repeated (710) for each screw in some embodiments of the invention.

It should be understood that in some embodiments of the invention, screw is not necessarily advanced (704) until ridge 112 abuts flange 404 but rather is advanced (704) only as far as required to place outlet 110 past flange 404 such that when tongue protrudes out of screw head 102 the flange 404 is bracket by tongue 108 and ridge 112. It should also be understood that implant 400 is merely exemplary and that spring screw 100 could be used with any implant or device adapted for use with the spring screw 100. For example, any implant or device with a flange in a screw hole which could be bracketed by ridge 112 and tongue 108.

Figure 8:
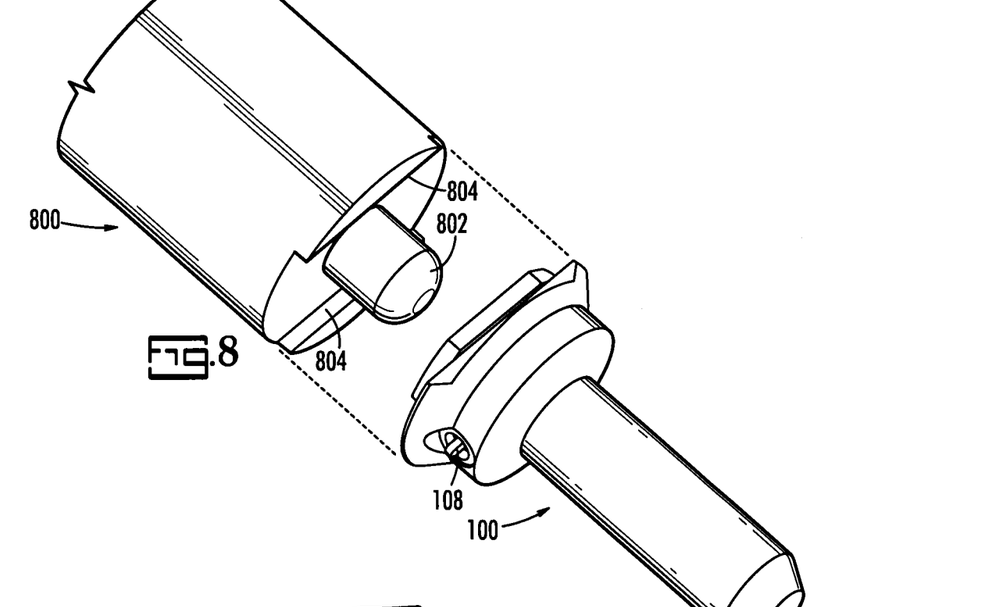
FIG. 8 is a perspective view of a spring screw and a tool used for locking and/or unlocking the spring screw, in accordance with an exemplary embodiment of the invention; and, FIG. 9 is a cross-sectional view of a spring screw and a tool used for locking and/or unlocking the spring screw flexing the spring member to unlock the spring screw, in accordance with an exemplary embodiment of the invention.

Referring to FIG. 8, a perspective view of spring screw 100 and a tool 800 used for locking and/or unlocking spring screw 100 is shown, in accordance with an exemplary embodiment of the invention. In an embodiment of the invention, tool 800 is adapted to act as a counterpart to tool slot 114 in spring screw head 102 to tighten and/or loosen spring screw 100 and/or to flex spring member 106 for locking spring screw 100 to implant 400. For example, a tool nub 802 is provided to tool 800 wherein tool nub 802 is sized to fit within tool slot 114 located in spring screw 100 and extend at least as far into tool slot 114 as is required to flex spring member 106 to floor 304, in an exemplary embodiment of the invention. Ridges 804 also be provided to tool 800 which assist in applying torque to spring screw 100 during tightening and/or loosening of the spring screw 100 from the implantation site. It should be understood, that tool 800 is merely an example of what could be used for flexing the spring member 106 and/or driving the screw into the implantation site. For example, any tool which fits within the slot (which as described above is variable in shape), is capable of extending into the slot far enough to flex the spring and/or is capable of applying torque to the screw sufficient for securing it to the implantation site, could be used.

Figure 9:
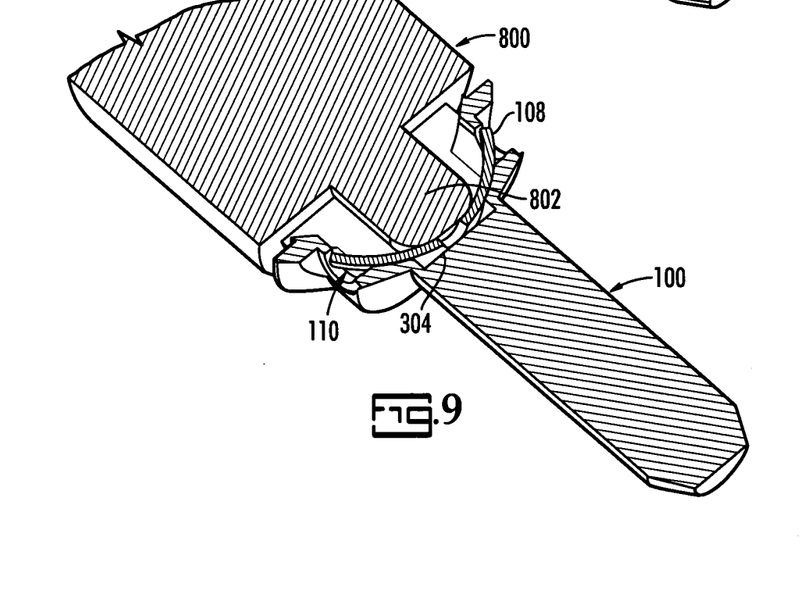

FIG. 9 is a cross-sectional view of spring screw 100 and tool 800 used for locking and/or unlocking spring screw 100 by flexing the spring member 106 to unlock the spring screw 100 into implant 400, in accordance with an exemplary embodiment of the invention. It can be seen that tool nub 802 of tool 800 exerts a force on spring member 106 such that it flexes towards floor 304. The flexing of spring member 106 causes its overall length relative to spring screw 100 to shorten, withdrawing the at least one tongue 108 into outlet 110, but not so far as to cause spring member 106 to become dislodged from the outlet 110. The retraction of spring member 106 allows for outlet 110 of spring screw 100 to be inserted into implant 400 past flange 404, in an embodiment of the invention.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting Those familiar with implantable devices and apparatuses and methods for attaching them to a patient's anatomy will appreciate that many modifications and substitutions can be made to the foregoing preferred embodiments of the present invention without departing from the spirit and scope of the present invention, defined by the appended claims.

What is claimed is:

1. A system for interlocking a screw and an implant wherein the screw has motion in only one degree of freedom, comprising:
    an implant provided with at least one screw hole provided with a flange having a sloped upper surface; and
    a screw having a cylindrical screw body with a head having an outer side wall constructed and arranged to fit within the implant screw hole, said head having a ridge formed along said outer side wall having a sloped lower surface sized to engage the implant flange and set at a level preventing said screw head from any further insertion into said implant screw hole, a tool slot formed within the outer side wall having a top opening formed along an upper surface of said head and extending to a floor with at least one outlet formed through said outer side wall adjacent to the floor; a planar spring member disposed within said tool slot having a tongue extendable through said outlet in a natural state and an enlarged portion or dimensions to prevent said spring member from sliding out of said outlet;
    wherein the tongue and the ridge form a flange slot adapted for receipt of the flange therein when the flexible spring member is in a natural un-flexed state; a tool adapted to be a counterpart to the tool slot; wherein the tool is provided with at least one ridge for providing torque to the screw for attaching the screw to the implantation site by driving said screw body into said implant screw hole while compressing said spring member.

2. A system according to claim 1, wherein the tool is provided with a tool hub for flexing the spring member upon insertion of the tool into the tool slot.

3. A system according to claim 1, wherein the one degree of freedom is around a central axis of the screw.

4. A spring screw for use in combination with an implant having at least one screw hole wherein an inner edge of the implant screw hole includes a flange, said spring screw comprising:
    a cylindrical screw body having a head with an outer side wall constructed and arranged to fit within the implant screw hole, said head having a ridge formed along said outer side wall sized to engage the implant flange, a tool slot formed within the outer side wall having a top opening formed along an upper surface of said head and extending to a floor with at least one outlet formed through said outer side wall adjacent to the floor;
    a planar spring member disposed within said tool slot having a tongue extendable through said outlet in a natural state and an enlarged portion or dimensions to prevent said spring member from sliding out of said outlet;
    wherein a tool placed within said tool slot drives said screw body into said implant screw hole, while compressing said spring member and flexing the spring member toward the tool slot floor causing the tongue of said spring member to retract into said outlet allowing insertion of the screw body into the implant screw hole, and upon removal of the tool the spring member extends through said outlet to maintain the ridge against the flange thereby locking said spring screw to the implant.

5. The spring screw according to claim 4, wherein the cylindrical screw body is threaded.

6. The spring screw according to claim 4, wherein the maximum flex of said spring member is no more than 20 thousandths of an inch.

7. The spring screw according to claim 4, wherein the tool slot and the spring member are formed as counterparts.

8. The spring screw according to claim 4, wherein the ridge has a lower surface which is sloped, increasing in size moving away from the cylindrical screw body constructed and arranged to engage the flange having a sloped upper surface.

9. The spring screw according to claim 4, wherein at least one of the flexible spring member, cylindrical screw body and screw head are constructed of at least one of titanium, stainless steel, cobalt chrome, ceramic, polymer, or PEEK Optima.

10. The spring screw according to claim 4, wherein the screw length along its central axis is 8.0 mm-60.0 mm.

11. The spring screw according to claim 4, wherein the screw head is 3.5 mm-9.0 mm in diameter.

* * * * *